United States Patent [19]

Bates

[11] Patent Number: 5,226,882
[45] Date of Patent: Jul. 13, 1993

[54] SINGLE-USE SYRINGE WITH NON-RETRACTABLE PISTON

[75] Inventor: William T. D. Bates, Willowbeck, England

[73] Assignee: Medi Pluc Tec, Medizinisch-Technische Handels-Gesellschaft mbH, Moers, Fed. Rep. of Germany

[21] Appl. No.: 821,936

[22] Filed: Jan. 16, 1992

[51] Int. Cl.$^5$ .............................................. A61M 5/00
[52] U.S. Cl. ...................................... 604/110; 604/228
[58] Field of Search ............... 604/110, 184, 218, 228, 604/229, 231, 236-238; 128/919

[56] References Cited

U.S. PATENT DOCUMENTS

| 4,973,309 | 11/1990 | Sultan | 604/228 |
|---|---|---|---|
| 5,078,686 | 1/1992 | Bates | 604/110 |
| 5,085,638 | 2/1992 | Farbstein et al. | 604/228 |
| 5,135,495 | 8/1992 | Arcusin | 604/110 |

FOREIGN PATENT DOCUMENTS

| 0304386 | 2/1989 | European Pat. Off. |  |
|---|---|---|---|
| 0329358 | 9/1989 | European Pat. Off. |  |
| 0336855 | 10/1989 | European Pat. Off. |  |
| 1500009 | 9/1967 | France | 604/110 |
| 2653340 | 4/1991 | France | 604/110 |
| 8809679 | 12/1988 | PCT Int'l Appl. | 604/218 |
| 9008565 | 8/1990 | PCT Int'l Appl. | 604/110 |
| 2015883 | 9/1979 | United Kingdom. |  |
| 2220143 | 1/1990 | United Kingdom. |  |

Primary Examiner—John D. Yasko
Assistant Examiner—Anthony Gutowski
Attorney, Agent, or Firm—Oblon, Spivak, McClelland, Maier & Neustadt

[57] ABSTRACT

A single-use syringe has a piston assembly sealingly slidable within a barrel. The piston assembly has a plunger (1) with a divergently tapered portion (4) and a resiliently deformable piston (2) with a through aperture (7), correspondingly tapered so that part of the tapered portion (4) may fit within the aperture, and a tapered skirt portion (6) adapted to surround a further part of the tapered portion (4). The through aperture is adapted to be plugged by the plunger. A locking ring (3) having a tapered aperture to surround said skirt portion is provided to hold the skirt (6) against the plunger end portion (4). When the plunger (1) is depressed within the barrel, the locking ring (3) is delayed by the wall of the barrel while the skirt (6) is pushed inwardly. Once the skirt (6) is unrestrained by the locking ring (3), outward movement of the plunger (1) will cause its end portion (4) to be pulled free from the piston (2). The piston (2) is thus non-retractable to prevent a second drawing-in of liquid.

9 Claims, 2 Drawing Sheets

SINGLE-USE SYRINGE WITH NON-RETRACTABLE PISTON

FIELD OF THE INVENTION

The present invention relates to a single-use syringe.

BACKGROUND OF THE INVENTION

One important factor in the transmission of certain diseases, most importantly HIV or AIDS, which can be transmitted through blood to blood contact, is the reuse of needles or syringes. Thus, a needle once used by a person infected with the AIDS virus or HIV is contaminated, and if the needle is then used by some other person, they will thereby become infected. This is particularly true of drug abusers, but may also be the case in other areas of syringe use.

One solution to the problem, in the form of a single-use syringe, has been disclosed in British patent application No. 8815355.6 published under serial No. GB-A-2220143A. The syringe disclosed is supplied in a fully depressed condition and, by virtue of a tapered locking ring surrounding a tapered portion of a piston, the piston may be withdrawn to fill the syringe. Inward pressure to dispense the contents disengages the locking ring from the piston, and therefore a second withdrawal is not possible.

However, desperate people may always try to overcome the above safety system. For example, they may attempt to push the piston and plunger back, either by inserting an elongate object through the nozzle opening or by forcing a fresh dose of injectant fluid into the syringe via the nozzle opening.

The present invention aims to provide a single-use syringe of a type which cannot easily be used a second time and therefore cannot contribute to the spread of diseases transmitted by contaminated blood or the like.

SUMMARY OF THE INVENTION

According to the present invention there is provided a single-use syringe comprising a piston assembly sealingly slidable within a barrel, the piston assembly having a plunger with a divergently tapered portion, a resiliently deformable piston having a tapered skirt portion adapted to surround at least a part of the plunger tapered portion, and a locking ring having a tapered aperture to surround the skirt portion and being in sliding frictional engagement with the barrel of the syringe; characterised in that the piston has a through aperture adapted to be plugged by the plunger, and the tapered skirt portion extends coaxially with the through aperture.

In a preferred embodiment, the plunger has a plug extending from the divergently tapered portion, the plug being dimensioned to fill a forward portion of the through aperture. The plug may be convergently tapered, and the through aperture may be dimensioned with a divergent taper corresponding to an end part of the plunger tapered portion and a convergent taper at the forward portion corresponding to the convergent taper of the plug.

Preferably the locking ring is a split ring.

The taper of the plunger tapered portion may comprise an angle in the region of 2 degrees.

The forward portion of the through aperture cooperable with the plug may have a diameter between one third and one quarter of the diameter of the piston.

EP-A-0336855 discloses a single-use syringe where the piston is held on the plunger by clip means very different to the locking ring and taper of the present invention. However, one embodiment of EP-A-0336855 shows a small hole through the piston which prevents the piston being re-set by the forcing of pressurised fluid through the needle aperture.

An embodiment of the present invention will now be more particularly described by way of example and with reference to the accompanying drawings, in which:

DETAILED DESCRIPTION OF THE INVENTION

Figure 1:
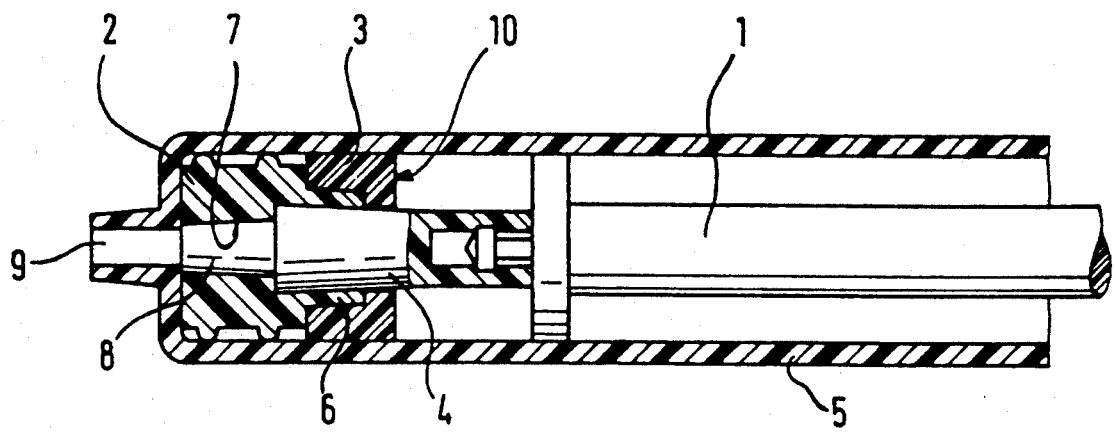
FIG. 1 shows schematically an end of the syringe with the piston assembly in an initial position prior to withdrawal.

A syringe comprises a conventional barrel 5 into which fits a piston assembly 10. As manufactured, the piston assembly is located at a fully inward disposition, i.e. immediately adjacent the closed end of a syringe barrel, to which a needle (not shown) would be fitted.

The piston assembly comprises a stem 1 which is manually operable at an outward end of the syringe, and which slides, non-sealingly, within the barrel 5. A plunger 4 attached at the inward end of the stem 1, tapers divergently at an angle in the region of 2 degrees for a portion of its length, beyond which it extends as a plug 8 of reduced diameter. A piston 2 is made from a resilient material such as rubber and forms a sliding sealing fit within the barrel 5. The piston 2 has an aperture 7 correspondingly shaped to accommodate an end of the tapered portion of the plunger 4 and the plug 8. Furthermore, a skirt 6, integral with the piston 2 surrounds the aperture 7 and continues the taper of the aperture. The ratio of diameters of the aperture 7 and piston 2 is between 1:3 and 1:4, and is preferably 1:3.5.

A locking ring 3, which is preferably a split ring of nylon or PVC or the like, surrounds the skirt 6. The aperture in the locking ring is correspondingly tapered to surround the skirt 6. The locking ring 3 is in frictional engagement with the internal surface of the barrel 5.

Figure 2:
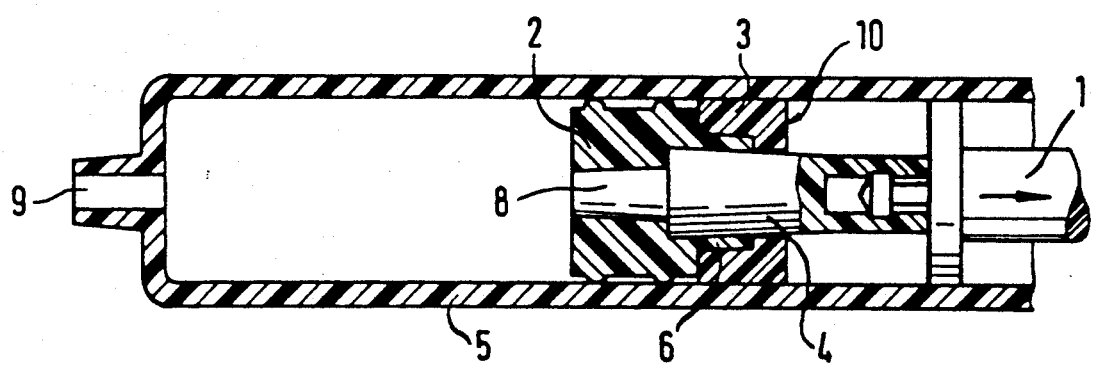
FIG. 2 shows the syringe of FIG. 1 during the piston withdrawal stroke.

As can be seen from FIG. 1, the piston assembly in its initial position is in the assembled condition. As the piston assembly is withdrawn (see FIG. 2) to introduce fluid into the syringe through an inlet part 9, the assembly remains in this assembled condition, the locking ring 3 forcing the resilient skirt 6 to grip around the tapered portion of the plunger 4.

Figure 3:
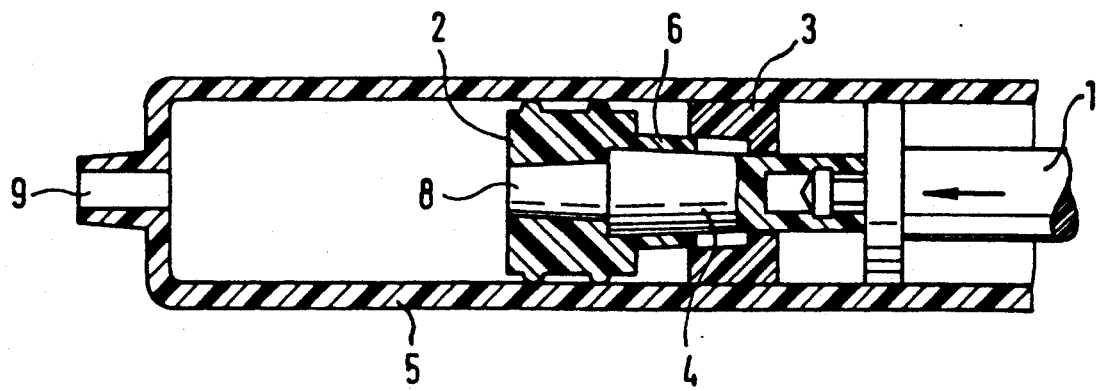
FIG. 3 shows the syringe during the injection stroke.
Figure 4:
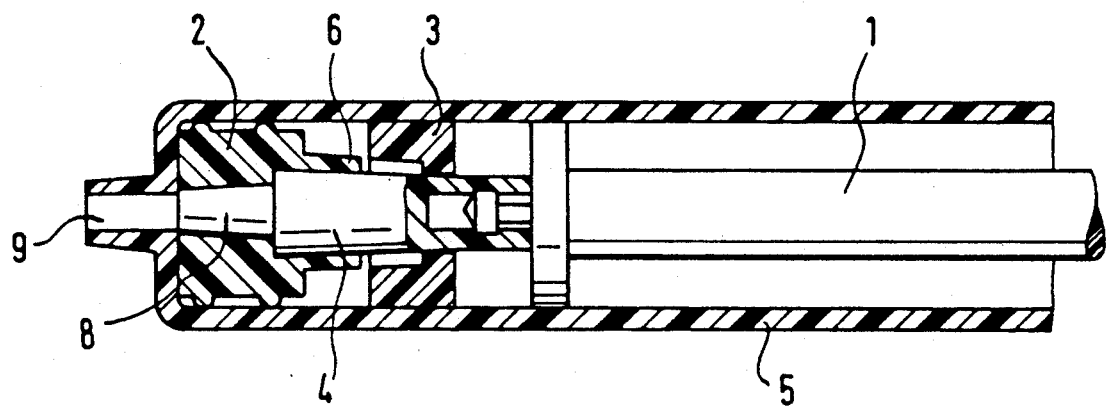
FIG. 4 shows the syringe at the end of the injection stroke.
Figure 5:
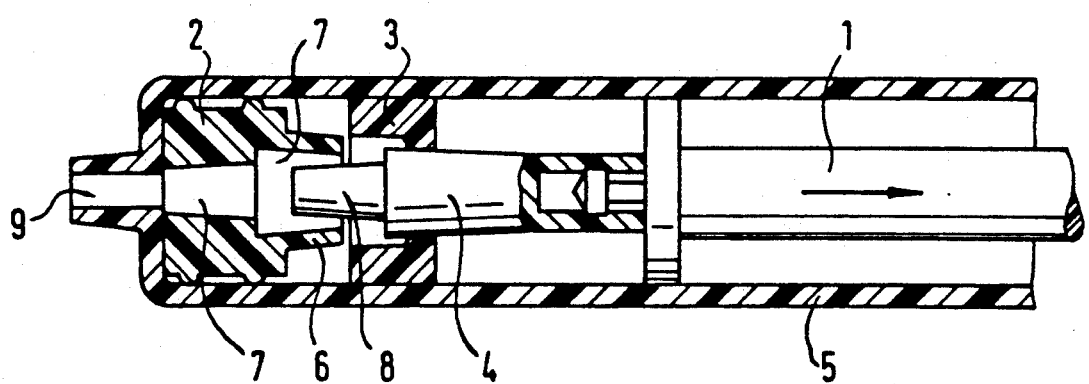
FIG. 5 shows the syringe during a subsequent attempted withdrawal stroke.

On the injection stroke (see FIG. 3) the locking ring is held back by its frictional engagement with the barrel while the plunger 4 forces the piston 2 inwardly. The locking ring 3 thus becomes disengaged from the skirt 6. This condition is maintained until the end of the injection stroke (see FIG. 4).

If an attempt is made to use the syringe a second time, withdrawal of the stem 1 causes the tapered plunger 4 to become disengaged from the resilient piston 2, since the skirt 6 deforms outwards to allow removal of the tapered plunger 4 from the aperture. Thus, the piston 2 remains at an innermost position. Even if the stem is forced inwardly, it is almost impossible to re-engage the tapered portion of the plunger within the skirt 6, since the skirt will have returned resiliently to its tapered shape and tends to crumple under the longitudinal pressure. Furthermore the locking ring 3 cannot be re-engaged around the skirt 6 without a special tool, and therefore the syringe cannot be reused.

On withdrawal of the stem, the plug 8 is pulled clear of the aperture 7. It is ideally convergently tapered at an angle of 2 degrees so that it releases more cleanly from the aperture 7, which is correspondingly tapered. Such withdrawal leaves aperture 7 as a through hole so that any attempt to force piston 2 back by injection of pressurised fluid will fail because the fluid will pass through the aperture and act only on the plunger 4, or will escape around the stem 1.

Even if some liquid is forced into the syringe, any attempt to expel it by inward motion of the stem 1 is more likely to cause the liquid to flow through the aperture 7.

Similarly, any attempt to force back the piston 2 by insertion of an elongate object or tool should fail because the object will pass through the aperture 7. The through part 7 should have an end diameter larger than the inlet aperture 9 through which fluid is drawn into the syringe, such that there is no ledge or shoulder which can be engaged by such a tool. Similarly the interior surface of the through aperture should have no forwardly directed ledges which might be engaged by such a tool. The forwardly convergent shape of the front portion of the through aperture also increases the difficulty of engaging any tool with the piston to push it backwards. Furthermore, the plunger would in any case not re-engage into skirt 6, because of the tapered shape of the skirt, as discussed above.

During assembly of the syringe, the piston assembly is inserted into the barrel 5 in what is effectively an injection stroke. Normally, this would disengage the locking ring 3 from the skirt 6, and therefore it must be held in position on the skirt during initial insertion. This can be achieved quite easily providing the stem 1 does not occupy the whole area of the barrel 5. For example, a cruciform cross section would be appropriate. In such a case, a mandrel comprising two rods could be placed alongside the stem 1 and inserted with it to hold the locking ring 3 in position. A split locking ring 3 is preferred since this renders assembly easier.

Alternatively, the plunger 4, piston 2 and locking ring 3 may be inserted as a unit separate from the stem 1, and the stem 1 may be inserted later and engage with a rear end of the plunger in a clip fit or any other suitable manner.

I claim:

1. A single-use syringe comprising a barrel having a forward end including an inlet port and a piston assembly including a plunger having a forwardly extending divergently tapered portion, a resiliently deformable piston having a front end facing the forward end of said barrel and an opposed rear end, a rearwardly extending, convergently tapered skirt potion on the rear end of said piston adapted to surround at least a part of said plunger tapered portion, and a locking ring having a forwardly extending, divergently tapered aperture to surround said skirt portion and being in sliding frictional engagement with said barrel of said syringe, said piston having a through aperture and said plunger having a plug part for plugging said through aperture, said tapered skirt portion extending rearwardly coaxially with said through aperture, said plug part extending forwardly from said divergently tapered portion of said plunger and being dimensioned to fill a forward portion of said through aperture, said plug part being convergently tapered in a forward direction and said through aperture having a rearwardly extending divergent taper corresponding to the forwardly extending convergent taper of said plug part.

2. The syringe of claim 1, wherein said locking ring is a split ring.

3. The syringe of claim 1, wherein the angle of taper of said plunger tapered portion is in the region of between 1 and 10 degrees with respect to the longitudinal axis of said plunger.

4. The syringe of claim 3, wherein said angle of taper is in the region of 1.5 to 5.0 degrees.

5. The syringe of claim 4, wherein said angle of taper is in the region of 2 degrees.

6. The syringe of claim 1, wherein said forward portion of said through aperture cooperable with said plug part has a diameter between one third and one quarter of the diameter of said piston.

7. The syringe of claim 1, including means for accommodating an elongate member for maintaining said locking ring in engagement with said tapered skirt portion during initial assembly of said syringe prior to use.

8. In a single-use syringe of the type including a barrel having a fluid port at one end, a piston slidable in the barrel, a plunger for exerting a longitudinal force on the piston to expel fluid from said barrel through said port, means for automatically disconnecting said plunger from said piston upon retraction of said plunger into said barrel following a single use of said syringe, and a normally closed through aperture in said piston coaxial with said fluid port and which is opened upon retraction of said plunger following a single use whereby an attempt to drive said piston inwardly by exerting fluid force through said port into said barrel is prevented as the fluid is relieved through said aperture; the improvement wherein the end of said through aperture adjacent said fluid port and said fluid port have cross sectional dimensions such that no portion of said piston adjacent said port overhangs said port to provide a ledge engageable by a tool inserted through said port for the purpose of retracting said piston into said barrel independently of said plunger, said port and through aperture being circular and coaxial, with the radius of the through aperture being greater than that of said port, said through aperture being also convergent in the direction of said fluid port thereby inhibiting the ability of a tool to engage said piston directly through said fluid port.

9. In a single-use syringe as claimed in claim 8 wherein the interior of said through aperture throughout its length has no forwardly directed ledges engageable by a tool inserted through said port.

* * * * *